United States Patent
Svensson et al.

(10) Patent No.: US 11,918,444 B2
(45) Date of Patent: Mar. 5, 2024

(54) ABSORBENT PAD WITH FIRST AND SECOND PRINTING PATTERN

(71) Applicant: Essity Hygiene and Health Aktiebolag, Gothenburg (SE)

(72) Inventors: Hanna Svensson, Bromölla (SE); Linda Rönn, Gothenburg (SE)

(73) Assignee: ESSITY HYGIENE AND HEALTH AKTIEBOLAG, Gothenburg (SE)

(*) Notice: Subject to any disclaimer, the term of this patent is extended or adjusted under 35 U.S.C. 154(b) by 0 days.

(21) Appl. No.: 17/595,441

(22) PCT Filed: May 29, 2019

(86) PCT No.: PCT/SE2019/050506
§ 371 (c)(1),
(2) Date: Nov. 17, 2021

(87) PCT Pub. No.: WO2020/242357
PCT Pub. Date: Dec. 3, 2020

(65) Prior Publication Data
US 2022/0142826 A1  May 12, 2022

(51) Int. Cl.
*A61F 13/513* (2006.01)
*A61F 13/475* (2006.01)
*A61F 13/15* (2006.01)

(52) U.S. Cl.
CPC .... *A61F 13/4758* (2013.01); *A61F 13/51394* (2013.01); *A61F 2013/15008* (2013.01);
(Continued)

(58) Field of Classification Search
CPC ........ A61F 2013/15243; A61F 13/5126; A61F 13/51394; A61F 13/4758
See application file for complete search history.

(56) References Cited

U.S. PATENT DOCUMENTS

D674,483 S  * 1/2013 Hood .......................... D24/125
8,492,609 B2  7/2013 Ecker et al.
(Continued)

FOREIGN PATENT DOCUMENTS

AR         065438 A1    6/2009
AR         066675 A1    9/2009
(Continued)

OTHER PUBLICATIONS

First Office Action dated Apr. 8, 2022, issued in the corresponding Chinese patent CN 201980096850.7, 14 pages including 7 pages of English Translation.
(Continued)

*Primary Examiner* — Susan S Su
(74) *Attorney, Agent, or Firm* — BUCHANAN INGERSOLL & ROONEY PC

(57) ABSTRACT

An absorbent pad including a fluid permeable topsheet, a backsheet, and an absorbent core. The absorbent core has a front portion, a rear portion and an intermediate portion, the front portion, the rear portion and the intermediate portion being of equal lengths, the absorbent core having a width varying no more than 20 mm along its length, wherein the topsheet in a printed central absorption zone, arranged over the front portion, the rear portion and the intermediate portion of the absorbent core, is provided with a first printed pattern including first print elements and the topsheet in a peripheral security zone arranged at least over the rear portion of the absorbent core, is provided with a second printed pattern including second print elements, wherein a degree of coverage of the second printed pattern is at least 30% greater than a degree of coverage of the first printed pattern.

23 Claims, 2 Drawing Sheets

(52) U.S. Cl.
CPC .............. *A61F 2013/15243* (2013.01); *A61F 2013/15463* (2013.01)

(56) References Cited

U.S. PATENT DOCUMENTS

| | | | |
|---|---|---|---|
| 8,536,401 B2 | 9/2013 | Veglio et al. | |
| D943,739 S * | 2/2022 | Alkmin | D24/124 |
| 2006/0129114 A1* | 6/2006 | Mason, Jr. | A61F 13/47254 604/361 |
| 2006/0142710 A1 | 6/2006 | Kigata et al. | |
| 2007/0043330 A1 | 2/2007 | Lankhof et al. | |
| 2008/0294139 A1 | 11/2008 | Ecker et al. | |
| 2009/0157021 A1 | 6/2009 | Sullivan et al. | |
| 2011/0028929 A1 | 2/2011 | Hopkins et al. | |
| 2013/0310784 A1 | 11/2013 | Bryant et al. | |
| 2014/0358106 A1* | 12/2014 | Tan | A61F 13/4752 604/385.01 |
| 2015/0057632 A1* | 2/2015 | Luzader | A61F 13/53747 604/385.04 |
| 2015/0094683 A1* | 4/2015 | Hashino | A61F 13/51104 604/385.101 |
| 2016/0051419 A1 | 2/2016 | Wasson et al. | |
| 2016/0113826 A1* | 4/2016 | Liu | A61F 13/84 604/367 |
| 2016/0278986 A1* | 9/2016 | Gross | A61F 13/537 |
| 2020/0093650 A1* | 3/2020 | Denti | A61F 13/51108 |

FOREIGN PATENT DOCUMENTS

| | | |
|---|---|---|
| AR | 066679 A1 | 9/2009 |
| CN | 101677884 A | 3/2010 |
| CN | 103298437 A | 9/2013 |
| CN | 106659606 A | 5/2017 |
| WO | 2008103650 A2 | 8/2008 |
| WO | 2014033578 A2 | 3/2014 |
| WO | 2018106157 A1 | 6/2018 |
| WO | 2019007531 A1 | 1/2019 |

OTHER PUBLICATIONS

International Preliminary Report on Patentability received for PCT Patent Application No. PCT/SE2019/050506, dated Dec. 9, 2021, 7 pages.
Office Action dated Apr. 4, 2022, issued in the Russian Patent Application No. 2021136803/03(077502), 17 pages including 4 pages of English Translation.
Office Action (Examination Report No. 1) dated Sep. 12, 2022, by the Australian Patent Office in corresponding Australian Patent Application No. 2019449028. (3 pages).
Office Action (Notice of Reasons for Rejection) dated Aug. 22, 2022, by the Chinese Patent Office in corresponding Japanese Patent Application No. 2021-570490, and an English Translation of the Office Action. (9 pages).
Office Action (Decision of Rejection) dated Dec. 5, 2022, by the Chinese Patent Office in corresponding hinese Patent Application No. 201980096850.7, and an English Translation of the Office Action. (10 pages).
The extended European Search Report dated Nov. 11, 2022, by the European Patent Office in corresponding European Application No. 19930663.0. (7 pages).
International Search Report (PCT/ISA/210) and Written Opinion (PCT/ISA/237) dated Jan. 22, 2020, by the Swedish Patent Office as the International Searching Authority for International Application No. PCT/SE2019/050506.
Office Action (Decision of Rejection) dated Mar. 20, 2023, by the Japanese Patent Office in corresponding apanese Patent Application No. 2021-570490, and an English Translation of the Office Action. (5 pages).
Office Action dated May 31, 2023, by the Colombian Patent Office in corresponding Colombian Patent Application No. NC2021/0015075, and an English Translation of the Office Action. (5 pages).
Office Action dated 2023, by the Egyptian Patent Office in corresponding Egyptian Patent Application, and an English Translation of the Office Action. (1 page).
Office Action dated Oct. 24, 2023, by the Argentinian Patent Office in corresponding Argentinian Patent Application No. 20200101461. (7 pages).

* cited by examiner

ABSORBENT PAD WITH FIRST AND SECOND PRINTING PATTERN

TECHNICAL FIELD

The present disclosure relates to an absorbent pad comprising a fluid permeable topsheet, a backsheet and an absorbent core and wherein the fluid permeable topsheet comprises a printed central absorption zone and a printed peripheral security zone.

BACKGROUND

The present disclosure relates to absorbent pads of the kind that is worn inside ordinary use.

The napkins or pads are generally provided with an absorbent core to receive and retain body liquids. The absorbent core may be shaped, such as for example having an hourglass shape or longitudinal edges being curved, for indicating correct positioning of the absorbent pad in the user crotch region. However, shaped absorbent core may be connected to increased material spill when cutting the absorbent core from material webs.

Absorbent pads may be provided with decorative print pattern on the topsheet and/or backsheet to enhance the appearance of the absorbent pad. Absorbent pads may also be provided with decorative pattern to enhance or visualize certain functions and characteristics of the pad.

An aim of the present invention is to provide an improved absorbent pad, which is simple and cost efficient to manufacture, has an enhanced appearance and provide improved handling by the user.

SUMMARY

One or more of the above objects may be achieved with an absorbent pad in accordance with an absorbent pad comprising a fluid permeable topsheet, a backsheet and an absorbent core including a first core layer being located between the topsheet and the backsheet, the absorbent core having first and second longitudinal side edges and front and rear end edges, the absorbent core having a front portion, a rear portion and an intermediate portion located between the front portion and the rear portion, as seen in a longitudinal direction of the absorbent pad, the front portion, the rear portion and the intermediate portion being of equal lengths, the absorbent core having a width varying no more than 20 mm along a length of the absorbent core extending in the longitudinal direction of the absorbent pad, wherein the topsheet in a printed central absorption zone, arranged over the front portion, the rear portion and the intermediate portion of the absorbent core, is provided with a first printed pattern comprising first print elements and that the topsheet in a peripheral security zone arranged at least over the rear portion of the absorbent core is provided with a second printed pattern comprising second print elements and in that a degree of coverage of the second printed pattern is at least 30% greater than a degree of coverage of the first printed pattern. Further embodiments are set out in the following description and in the drawings.

The absorbent pad as disclosed herein comprises a fluid permeable topsheet, a backsheet and an absorbent core including a first core layer being located between the topsheet and the backsheet. The absorbent core has first and second longitudinal side edges and front and rear end edges. The absorbent core in its longitudinal direction has a front portion, a rear portion and an intermediate portion located between the front portion and the rear portion, the front portion, the rear portion and the intermediate portion being of equal lengths. The absorbent core may have a width varying no more than 25 mm along a length of the absorbent core extending in the longitudinal direction of the absorbent core. The topsheet may be provided with a printed central absorption zone, arranged over the front portion, the rear portion and the intermediate portion of the absorbent core. The printed central absorption zone may be provided with a first printed pattern comprising first print elements. The topsheet may furthermore be provided with a printed peripheral security zone arranged at least over the rear portion of the absorbent core. The printed peripheral security zone may be provided with a second printed pattern comprising second print elements and a degree of coverage of the second printed pattern may be at least 30% greater than a degree of coverage of the first printed pattern.

The term "absorbent pad" refers to products that are placed against the skin of the wearer to absorb and contain body exudates, like urine, feces and menstrual fluid. The invention mainly refers to disposable absorbent pads, which means articles that are not intended to be laundered or otherwise restored or reused as a sanitary article. Examples of disposable absorbent pads include feminine hygiene products such as sanitary napkins, panty liners, sanitary panties and feminine inserts; diapers for infants and incontinent adults; incontinence pads; diaper inserts and the like.

The degree of coverage of the print may be measured by measuring over an area of 20×20 mm within the respective printed pattern, in an area relatively centralized within the pattern.

The degree of coverage of the second printed pattern may be at least 40% greater than the degree of coverage of the first printed pattern. Optionally, the degree of coverage of the second printed pattern may be at least 50% greater than the degree of coverage of the first printed pattern. The degree of coverage of the second printed pattern may furthermore be at least 60%, 80%, 200% or 300% greater than the degree of coverage of the first printed pattern. Optionally, the degree of coverage of the second printed pattern may be up to the coverage of the first printed pattern multiplied by 10.

When producing absorbent cores for absorbent pads, webs of absorbent material, such as for example fluff fibers, fluff fibers mixed with superabsorbent particles, nonwoven material or any other absorbent material suitable for use in an absorbent core in an absorbent pad, may be cut into the predetermined shape. For rectangular absorbent core there is in generally no spillage of material, however for shaped absorbent core the spillage may be relatively high. Hence with an absorbent core having a width of the absorbent core in front portion and intermediate portion varies no more than 25 mm along a length of the absorbent core extending in the longitudinal direction of the absorbent core, the material spillage is low.

It is also possible to produce absorbent cores for absorbent articles based on a core forming drum which comprises a rotating cylinder. A number of core molds may be arranged along the circumference of a cylinder. A supply of fibres of cellulosic fluff pulp, optionally mixed with superabsorbents may be arranged above the drum in a manner so that said material fills the core molds as they pass the position of the supply during rotation of the cylinder. In order to assist this procedure, a vacuum chamber including a vacuum source may be arranged in the cylinder so as to draw air through the core molds.

The width of the absorbent core in the front portion and the intermediate portions may vary from 0 mm up to 25 mm along a length of the absorbent core extending in the longitudinal direction of the absorbent core, or vary from 0 mm up to 25 mm along the entire length of the absorbent core extending in the longitudinal direction of the absorbent core. Such a varying width may provide an absorbent core for which the material spillage is low during production but which still may provide enhanced fitting of the pad in the crotch, such as for example if the absorbent core has a varying transverse width with a portion arranged in a rear section of the front portion, or alternatively in a front section of the intermediate portion, above the core being narrower than the transversal width of the rest of the absorbent core.

When using absorbent pads during the night and when the absorbent pads are exposed for heavier insults, users may often feel worried that the pads have enough absorption capacity and that the pads may leak in a rear portion of the absorbent pad, especially during night when the user is laying down. The absorbent pad is provided with a printed central absorption zone comprising a first printed pattern and with printed peripheral security zone comprising a second printed pattern. The printed peripheral security zone is arranged at least over the rear portion of the absorbent core and the degree of coverage of the second printed pattern is at least 30% greater than the degree of coverage of the first printed pattern, this has been found to provide the user's with a visual impression of a high absorbent central portion and an extensive peripheral rear portion giving the users a sense of security.

The printed peripheral security zone comprising the second printed pattern may extend over the front portion of the absorbent core and the rear portion of the absorbent core. Optionally, the peripheral security zone may extend over the front portion, the intermediate portion and the rear portion of the absorbent core. The peripheral security zone may extend outside the central absorption zone in the front portion, the intermediate portion and the rear portion, thereby framing the central absorption zone. The peripheral security zone may extend outside the central absorption zone and framing completely the central absorption zone. The topsheet may cover the absorbent core with the first and the second pattern.

Optionally, the peripheral security zone may mirror the shape of the central absorption zone in the intermediate portion. Optionally the peripheral security zone may mirror the shape of the outer contour of the pad in the intermediate zone.

Optionally, the printed peripheral security zone has a rear end length $l_r$, as measured along a centre line of the absorbent pad extending in the longitudinal direction between the print element provided closest to the rear end edge of the absorbent pad and a transition between the printed peripheral zone and the printed absorption zone arranged over the rear portion of the absorbent core, and a front end length $l_f$, as measured along a centre line of the absorbent pad extending in the longitudinal direction between the print element provided closest to the front end edge of the absorbent pad and a transition between the printed peripheral zone and the printed absorption zone arranged over the front portion of the absorbent core, and wherein the $l_r > l_f$, optionally wherein $l_r$ is at least 30% longer than $l_f$.

Optionally, the printed peripheral security zone has a rear end length $l_r$, as measured along a centre line of the absorbent pad extending in the longitudinal direction between the rear end edge of the absorbent core and a transition between the printed peripheral zone and the printed absorption zone arranged over the rear portion of the absorbent core, and a front end length, as measured along a centre line of the absorbent pad extending in the longitudinal direction between the front end edge of the absorbent core and a transition between the printed peripheral zone and the printed absorption zone arranged over the front portion of the absorbent core, and wherein the $l_r > l_f$, optionally wherein $l_r$ is at least 30% longer than $l_f$.

The first sparser printing pattern provided in the printed absorption zone gives the wearer a sense of security with a high absorbent central portion and an extensive peripheral security zone provided around the central absorption zone. To feel confident that the absorbent pad has a sufficient absorbent capacity and does not leak may improve the sleep of the wearer and the confidence during the day.

The second printed elements may have a larger mean size than the first printed elements. By this is meant that for example 60% of the printed elements in the second printed pattern have a larger mean size than the first printed elements in the first pattern. This has also been found to promote the impression of a large size peripheral zone of the topsheet and the absorbent pad.

The first printed elements in the central absorption zone may be absorption enhancement indicating elements, such as printed dots having a diameter of from 0.2 mm to 3.0 mm.

It has been seen by the present inventors that a repeating pattern of small-sized dots, squares, triangles or a net-like pattern may provide the impression of a highly liquid-receiving structure.

The coverage of the first printed pattern in the central absorption zone may be 5% or more, optionally between 5% and 25%.

The coverage of the second printed pattern in the peripheral security zone may be 10% or more, optionally between 10% and 55%.

The printed central absorption zone may have a varying transverse width, with a portion arranged in a transitional area of the front portion and the intermediate portion of the core being narrower than the transversal width of the rest of the printed central absorption zone and wherein the transverse width in the most narrow section is from 40% to 80% of a widest section of the absorbent core.

When measuring the width of the printed central absorption zone, a line is drawn around the first printed pattern along the outermost first printed elements and thereby forming an outer periphery.

The fact that the absorbent core has a rectangular or modified rectangular shape within at least the front and the intermediate portion may lead to that the user has greater difficulty in identifying the front and the rear part of the absorbent pad. However, when the transverse width of the printed central absorption zone is more narrow in a portion of the topsheet being arranged over a transition area of the front portion and the intermediate portion, this gives the user the impression of a shaped article and thereby promotes correct placement of the article, such as which part of the absorbent pad that is intended to be arranged at level with the tendons and also the intended direction of the absorbent pad.

A transition area between the front and the intermediate portion may be seen as an area extending from a transition line arranged at a transition between the front portion and the intermediate portion and 20 mm, or 10 mm in a direction towards the front end edge of the absorbent core and 20 mm, or 10 mm in a direction towards the rear end edge of the absorbent core.

The printed central absorption zone may be enclosed by a printed contour line(s) following the contour of the central absorption zone. Such print further accentuates the contour of the central absorption zone and thereby further accentuates which part of the absorbent pad that is intended to be arranged at level with the tendons and thus the intended direction of the absorbent pad. Such printed contour line(s) may be seen as forming a transition between the printed absorption zone and the printed peripheral security zone.

The printed central absorption zone may have a varying transverse width, with a transition area arranged between the rear portion and the intermediate portion of the core being wider than the transversal width of the rest of the printed central absorption zone.

The printed contour line(s) may comprise a first and a second intermediate printed contour line extending in the longitudinal direction on a respective side of the printed central absorption zone. The first and the second intermediate printed contour line may each have a curved shape following the shape of the printed central absorption zone, and the first and the second intermediate printed contour line may have a respective first and second front end portion and a respective first and the second rear end portion.

The printed contour line(s) may include a U-shaped, modified U-shaped, W-shaped, modified W-shaped, V-shaped or modified V-shaped contour line rear section enclosing a rear transverse end of the printed central absorption zone and having contour line rear section first and second legs extending at each side of the printed central absorption zone in the longitudinal direction toward the front end edge of the absorbent core. The rear end length $l_r$ of the printed peripheral security zone may be measured along a centre line of the absorbent pad extending in the longitudinal direction and between the rear end edge of the absorbent core and the contour line rear section.

The contour line rear section first and second legs may be arranged outwardly of, and overlapping with the respective first and the second rear end portion of the first and a second intermediate printed contour line, as seen in the transverse direction. This has been seen to enhance the impression of a broader rear portion and provide the user with the impression of a broad peripheral security zone.

The peripheral security zone may have a rear end length being at least 40% of the length of the rear portion of the absorbent core, as measured along a centre line of the absorbent pad extending in the longitudinal direction between the rear end edge of the absorbent core and the contour line rear section. This has been found to visualize the length of the rear portion of the absorbent pad and provide the user with a sense of security with a long rear portion providing protecting against leakage from the rear portion.

The contour line rear section may be provided with a rear end direction indicator, providing indication to the wearer of the intended direction of the absorbent pad, thereby promoting correct user positioning of the absorbent pad. The rear end direction indicator may for example be in the form of a concave part of the contour line rear section directed towards a front edge of the absorbent pad, an arrow or the like. The contour line rear section may have the shape of a modified W-shape, a U-shape, a modified U-shape or a W-shape.

The contour line front section may be provided with a front end direction indicator, providing indication to the wearer of the intended direction of the absorbent pad, thereby promoting correct user positioning of the absorbent pad. The contour line front section may include a U-shaped, modified U-shaped, V-shaped or modified V-shaped contour line front section enclosing a front transverse end of the central absorption zone and having contour line front section first and second legs extending at each side of the central absorption zone toward the rear end edge of the absorbent core. The front end length $l_f$ of the printed peripheral security zone may be measured along a centre line of the absorbent pad extending in the longitudinal direction, and between the front end edge of the absorbent core and the contour line front section. However, if the print pattern may be located also outwardly the front edge of the absorbent core, the length $l_f$ of the printed peripheral security zone is measured between the print element(s) outwardly the front edge of the absorbent core which is located closest to the front edge of the absorbent pad and the contour line front section. Also, if the print pattern does not have a contour line front section, the length $l_f$ of the printed peripheral security zone is instead measured to the first printed elements 16 which is located closest to the front edge of the absorbent pad, in the first printed pattern 15.

The contour line front section first and second legs are arranged outwardly of, and overlapping with the respective first and the second front end portion of the first and a second intermediate printed contour line, as seen in the transverse direction. This may provide the impression of a larger size front section with a narrower waist section of the contour line arranged below the front section and gives the impression of a shaped absorbent core with a wider front section.

The contour line front section may be provided with a front end direction indicator, providing indication to the wearer of the intended direction of the absorbent pad, thereby promoting correct user positioning of the absorbent pad. The front end direction indicator may for example be in the form of a concave part of the contour line front section directed towards a front edge of the absorbent pad, an arrow or the like.

Optionally, an elastic element is disposed between the fluid permeable topsheet and the backsheet outside of the respective longitudinal core side edges. The respective elastic elements may each extend along at least a part of the front portion and along at least 30% of the intermediate portion of the absorbent core.

The fact that the elastic elements are disposed between the fluid permeable topsheet and the backsheet outside of the respective longitudinal core side edges and over at least a part of the front portion and over at least 30% of the intermediate portion, provides the longitudinal edges at the front and intermediate portions of the absorbent core with elasticity which helps shaping the absorbent pad to a cup-shape in a transition area between the front portion of the intermediate portion. This has been seen to reduce lateral leakage significantly. Furthermore, as the absorbent pad is generally rectangular, the fact that the elastic elements are arranged outwardly and along the longitudinal edge of the front portion of the absorbent core, provides indication of correct placement of the absorbent pad with respect to the front and rear sections of the absorbent pad. The fact that the elastic elements are closer towards the front end edge as compared to the rear end edge provides a visual cue to the user of a longer absorbent pad having a longer rear end. This may provide the user of a sense of security with respect to leakage from the absorbent pad rear end. Night pads user may often feel worried that the products will leak at the rear end. This may cause troubles sleeping due to for example fear of sleeping in certain positions or waking up repeatedly during the night to ensure that there has been no leakage from the pad.

The area between the fluid permeable topsheet and the backsheet and outside of the respective longitudinal core side edges of the rear portion of the core may be free from elastic elements.

The fact that elastic elements are disposed between the fluid permeable topsheet and the backsheet outside of the respective longitudinal core side edges and over at least a part of the front portion and over at least 30% of the intermediate portion, provides the front portion of the absorbent core with elasticity which helps shaping the absorbent pad in the front end has been seen to reduce lateral leakage. Furthermore, as the absorbent pad is generally rectangular, the fact that the elastic elements are arranged outwardly and along the longitudinal edge of the front portion of the absorbent core, provides indication of correct placement of the absorbent pad with respect to the front and rear sections of the absorbent pad.

The respective elastic elements may optionally extend over at least 40% of the intermediate portion, optionally over at least 50% of the intermediate portion or optionally at least 60% of the intermediate portion.

The absorbent pad may have an interspace free from absorbent material located between the respective elastic elements and the absorbent core.

The topsheet may be attached directly to the backsheet in the interspace free from absorbent material located between the respective elastic elements and the absorbent core.

Optionally, a width of the first core layer arranged in the front portion and the intermediate portion of the absorbent core varies 0-20 mm or less along a length of the first core layer extending in the longitudinal direction. Optionally the first core layer varies 0-20 mm or less along the entire length of the first core layer.

The absorbent core may comprise a second core layer located between the topsheet and the backsheet. Optionally the second core layer is located between the topsheet and first core layer.

The second core layer may extend over at least a part of the front portion and the intermediate portion of the first core layer. The second core layer may have a length which is shorter than the first core layer.

The respective elastic elements extend laterally outboard a widest portion, as seen in a transverse direction, of the front portion of the second core layer.

Optionally, a width of the second core layer varies 0-25 mm along a length of the second core layer, or 0-25 mm along the entire length of the second core layer. Optionally the width of the second core layer varies less than the width of the first core layer, for example not more than 25 mm, 10 mm, 5 mm, or 2 mm along a length of the second core layer or along the entire length of the second core layer.

The absorbent core may be generally rectangular. The first core layer may be generally rectangular. The second core layer may be generally rectangular. By generally rectangular is meant that the width of the core does not vary more than 3 mm along its length. The absorbent core may have rounded front and end edges and these rounded edges are not considered as part of the core length when defining "generally rectangular".

Optionally, each of the areas outside of the respective longitudinal core side edges in the rear portion of the first absorbent layer and between the topsheet and the backsheet are free from elastic elements.

A thickness of the absorbent pad in the area where the absorbent core comprises a first and a second core layer could for example be 4 mm or more, such as from 4 mm to 25 mm, the thickness measurement being made at a load of 0.5 kPa with a 5×5 cm square plate.

The elastic elements may have an extension in the longitudinal direction of from 20% to 50% of the total length of the absorbent core, as measured when the elastic elements is in a relaxed condition.

The length in the longitudinal direction between the front end edge of respective elastic element and the front end edge of the absorbent core may be not more than 66% of the total length of the front portion of the absorbent core.

Optionally, the length in the longitudinal direction between the front end edge of respective elastic element and the front end edge of the second core layer may be not more than 20% of the total length of the front portion of the absorbent core.

Optionally, the backsheet is provided with adhesive means on a garment-facing side thereof.

The absorbent pad may be an over-night pad.

BRIEF DESCRIPTION OF THE DRAWINGS

The present invention will be further explained hereinafter by means of non-limiting examples and with reference to the appended drawings wherein.

DETAILED DESCRIPTION

Figure 1:
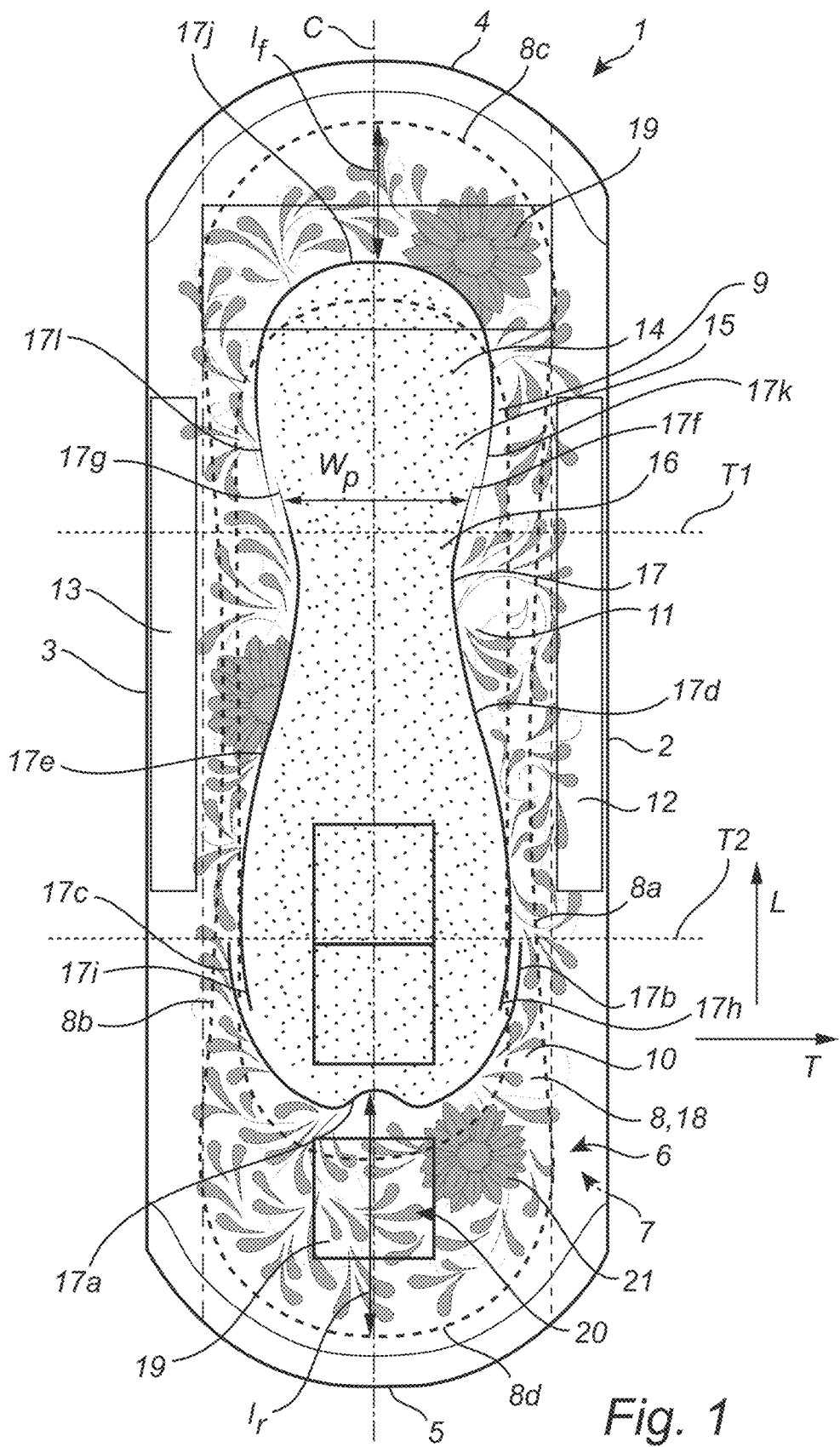
FIG. 1 shows a top plan view of an absorbent pad provided with a printed pattern as disclosed herein as disclosed herein.

The invention will be described more closely below by reference to an exemplary embodiment. The invention may however be embodied in many different forms and should not be construed as limited to the embodiments set forth in the drawings and the description thereto.

FIG. 1 schematically shows an absorbent pad 1 according to the present disclosure. The absorbent pad 1 has first and second longitudinal pad side edges 2,3 and front and rear pad end edges 4,5. The absorbent pad 1 comprises a fluid permeable topsheet 6, a backsheet 7 and an absorbent core 8 including a first core layer 18 being located between the topsheet 6 and the backsheet 7. The absorbent core 8 has a first and a second longitudinal side edge 8a,8b and a front and a rear end edge 8c,8d. The absorbent core 8 has in its longitudinal direction L a front portion 9, a rear portion 10 and an intermediate portion 11 located between the front portion 9 and the rear portion 10. The front portion 9, the rear portion and the intermediate portion 11 are of equal lengths, i.e., each representing ⅓ of the length of the absorbent core, such that a transition T1 between the front portion and the intermediate portion is arranged ⅓ of the total length of the absorbent core 8 from the core front end edge 8c, and a transition T2 between the intermediate portion and the rear portion is arranged ⅓ of the total length of the absorbent core 8 from the core rear end edge 8d.

The absorbent pad 1 has a topsheet 6 which is printed with a first printing pattern 15 and a second printing pattern 20. The topsheet 6 may include one or several layers and may also include a so-called acquisition layer. The print may be provided on any of these layers. The topsheet 6 is printed with a first printed pattern 15 forming a printed central absorption zone 14 extending over the front portion 9, the rear portion 10 and the intermediate portion 11 of the absorbent core 8. The printed central absorption zone 14 is provided with the first printed pattern 15 comprising first print elements 16, here in the form of dots. The central absorption zone 14 is enclosed by printed contour lines 17 following the contour of the central absorption zone 14. The printed contour lines 17 includes a contour line rear section 17a enclosing a rear transverse end of the central absorption zone 14 and having contour line rear section first and second legs 17b,17c extending at each side of the central absorption zone 14 in the longitudinal direction (L) toward the front end edge 8c of the absorbent core 8. In FIG. 1 the contour line rear section 17a has the shape of a modified W-shaped contour line rear section 17a where at the portion coinciding with a centre line C of the absorbent pad 1 has a concave part, as seen from the rear end edge 5 and towards the front end edge 4 of the absorbent pad 1. However, contour line rear section 17a may alternatively have a U-shape, modified U-shape or a W-shape. The printed concave part of the contour line rear section 17a has been found to provide indication to the user as to which part of the absorbent pad 1 is the rear part and which part is the front part of the absorbent pad. The printed contour lines 17 further comprises a first and a second intermediate printed contour line 17d,17e extending in the longitudinal direction L on a respective side of the printed central absorption zone 14 and over the front portion 9, the intermediate portion 11 and the rear portion 10 of the absorbent core 8. As illustrated in the figure, the first and the second intermediate printed contour line 17d,17e each has a curved shape following the shape of the central absorption zone 14. The first and the second intermediate printed contour line 17d,17e has a respective first and second front end portion 17f,17g and a respective first and the second rear end portions 17h,17i. The first and the second rear end portions 17h,17i of the first and the second intermediate printed contour line 17d,17e are arranged inwardly of and overlapping with the respective contour line rear section first and second legs 17b,17c, as seen in the transverse direction T.

In FIG. 1, the printed contour lines 17 further include a U-shaped contour line front section 17j enclosing a front transverse end of the central absorption zone 14 and having contour line front section first and second legs 17k,17l extending at each side of the central absorption zone 14 in the longitudinal direction (L) toward the rear end edge 8d of the absorbent core 8. The first and the second front end portions 17f, 17g of the first and the second intermediate printed contour line 17d,17e are arranged inwardly of and overlapping with the respective contour line front section first and second legs 17k,17l, as seen in the transverse direction T.

The printed central absorption zone 14 has a varying transverse width w p with a narrow portion of the printed central absorption zone 14 arranged over a part of the topsheet being arranged above the transition area between the absorbent core front portion 9 and the absorbent core intermediate portion 11, i.e., in a rear section of the front portion 9, or alternatively in a front section of the intermediate portion 11. The narrow portion being narrower than the transversal width w p of the rest of the printed central absorption zone 14 and wherein the transverse width w p in the most narrow section is from 40% to 80% of a widest section of the absorbent core 8.

The topsheet 6 is furthermore provided with a printed peripheral security zone 19 provided around the printed central absorption zone 14 and over the front portion 9, the intermediate portion 11 and the rear portion 10 of the absorbent core 8. The printed peripheral security zone 19 comprises a second printed pattern 20 comprising second print elements 21, here in the form of a floral pattern. A degree of coverage of the second printed pattern 20 is at least 30% greater than a degree of coverage of the first printed pattern 15. The printed peripheral security zone 19 has a rear end length $l_r$, as measured between the rear end edge 8d of the absorbent core 8 and the contour line rear section 17a, along the centre line C of the absorbent pad 1. However, if the print pattern may be located also outwardly the rear edge of the absorbent core, the length $l_r$ of the printed peripheral security zone is measured between the printed element(s) outwardly the rear edge of the absorbent core which is located closest to the rear edge of the absorbent pad and the contour line rear section. Also, if the print pattern does not have a contour line rear section, the length $l_r$ of the printed peripheral security zone is instead measured to the first printed elements 16 which is located closest to the rear edge of the absorbent pad, in the first printed pattern 15.

The printed peripheral security zone 19 has a rear end length $l_r$, as measured between the rear end edge 8d of the absorbent core 8 and the contour line rear section 17a, along the centre line C of the absorbent pad 1. The rear end length $l_r$ of the printed peripheral security zone 19 is about 65% of the length of the rear portion 10 of the absorbent core 8, as measured along a centre line of the absorbent pad 1 extending in the longitudinal direction L. The rear end length $l_r$ of the printed peripheral security zone 19 may be about 50% or more of the length of the rear portion 10 of the absorbent core 8.

The printed peripheral security zone 19 in FIG. 1 has a front end length $l_f$, as measured between the front end edge 8c of the absorbent core 8 and the contour line front section 17j, along the centre line C of the absorbent pad 1. The front end length $l_f$ of the printed peripheral security zone 19 is about 30% of the length of the rear portion 10 of the absorbent core 8, as measured along a centre line of the absorbent pad 1 extending in the longitudinal direction L. The rear end length $l_r$ of the printed peripheral security zone 19 may be about 30% or longer compared to the front end length $l_f$ of the printed peripheral security zone 19.

Figure 2:
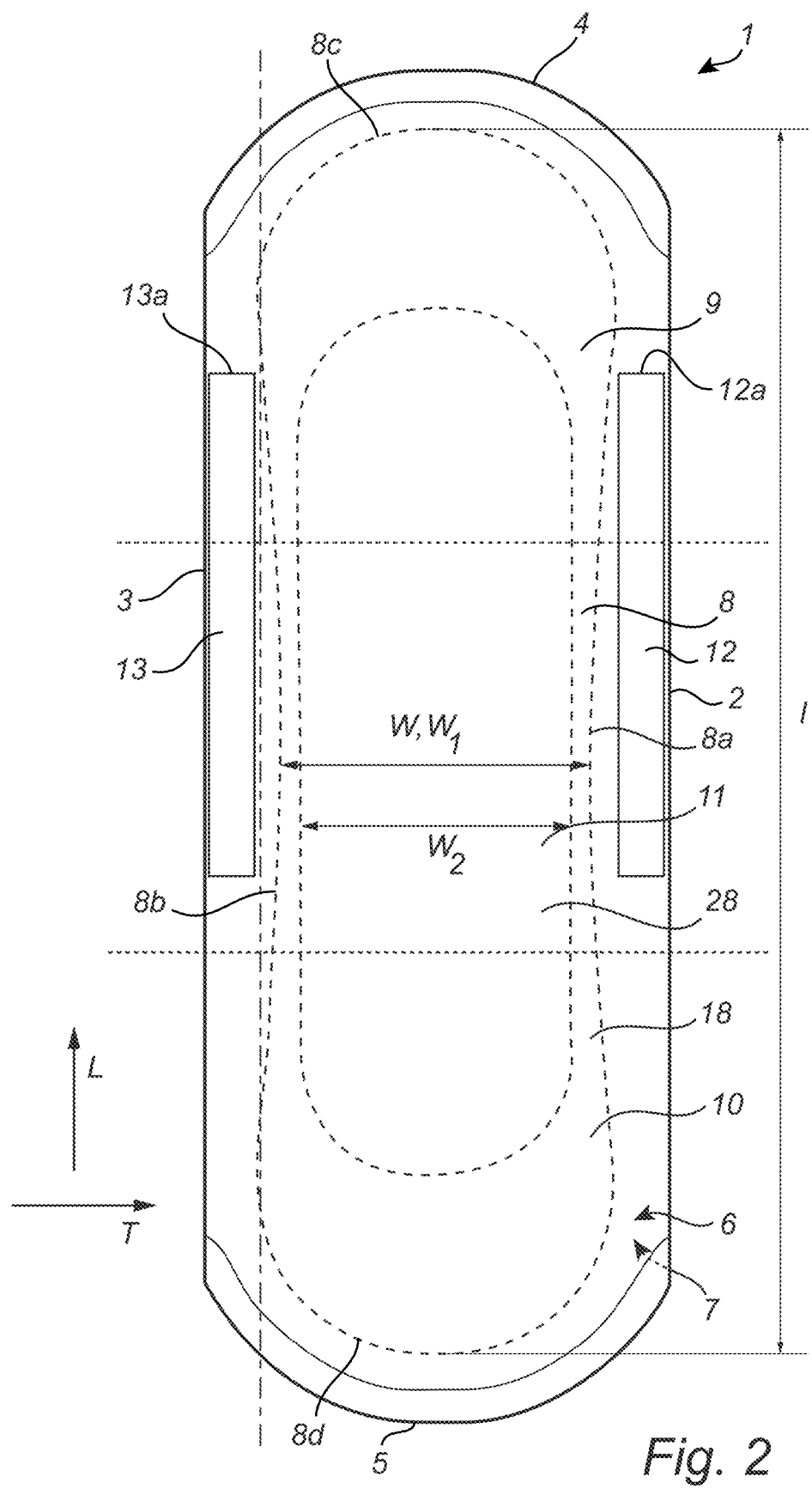
FIG. 2 shows a top plan view of an absorbent pad.

The absorbent pad 1 illustrated in FIG. 2 corresponds to the absorbent pad 1 illustrated in FIG. 1, but without the print on the topsheet. Outside each respective longitudinal core side edges 8a,8b the absorbent pad 1 is provided with elastic elements 12,13. The elastic elements 12,13 are disposed between the fluid permeable topsheet 6 and the backsheet 7.

The absorbent core 8 furthermore includes a second core layer 28 located between the topsheet 6 and the first core layer 18. The second core layer 28 has a smaller surface area than the first core layer 18 and the second core layer 28 has a length which is shorter than the length of the first core layer 18 and a first and a second longitudinal side edge of the second core layer 28 are provided laterally inwards of the respective first and second longitudinal side edges 8a,8b of the absorbent core 8.

The absorbent core 8 illustrated in FIGS. 1 and 2 has a slightly curved shape, but a width w of the absorbent core 8 in the front portion 9 and the intermediate portion varies no more than 25 mm, such as not more than 10 mm, along a length l of the absorbent core 8 extending in the longitudinal direction L of the absorbent core 8. This means that a widest width of the absorbent core is not more than 25 mm, optionally 10 mm, wider than the narrowest width of the absorbent core, as measured in a transverse direction T of the absorbent pad 1. As the contour of the first core layer 18 corresponds to the contour of the absorbent 8, the first core layer 18 has a slightly curved shape with a width $w_1$ not varying more than 25 mm, such as not more than 10 mm, along a length l of the first core layer 18 extending in the longitudinal direction L of the absorbent core 8. The second core layer 18 also has a width w$_2$ which does not vary more than 25 mm, such as not more than 10 mm, along a length l of the first core layer 18 extending in the longitudinal direction L of the absorbent core 8. The width w$_2$ of the second core layer 28 may vary less than the width w$_1$ of the first core layer 18, such than not more than 5 mm along a length l of the second core layer 28 extending in the longitudinal direction L of the absorbent core 8.

The topsheet 6 may include or consist of fibrous nonwoven layer(s) being spunbonded, meltblown, carded, hydroentangled, wetlaid etc. Suitable nonwoven materials can be composed of natural fibers, such as wood pulp or cotton fibres, synthetic thermoplastic fibres, such as polyolefins, polyesters, polyamides and blends and combinations thereof or from a mixture of natural and synthetic fibres. The materials suited as topsheet materials should be soft and non-irritating to the skin and be readily penetrated by body fluid, such as urine or menstrual fluid. The topsheet material may essentially consist of synthetic thermoplastic fibers, such as polyolefins, polyesters, polyamides and blends and combinations thereof. The synthetic fibers may be monocomponent fibers, bicomponent fibers or multicomponent fibers including polyesters, polyamides and/or polyolefins such as polypropylene and polyethylene.

The absorbent core 8 may be of any conventional kind. Examples of commonly occurring absorbent materials are cellulosic fluff pulp, tissue layers, highly absorbent polymers (so called superabsorbents), absorbent foam materials, absorbent nonwoven materials or the like. It is common to combine cellulosic fluff pulp with superabsorbents in an absorbent structure. It is also common to have absorbent structures comprising layers of different material with different properties with respect to liquid acquisition capacity, liquid distribution capacity and storage capacity. Components for improving various properties of the absorbent core can also form part of the absorbent core. Examples of such component are binding fibers, various types of fluid-dispersing layers or fibers, dimensionally stabilising component, reinforcing fibers or like. This is well-known to the person skilled in the art and does therefore not have to be described in detail. The thin absorbent bodies, which are common in today's sanitary articles, often, comprise a compressed mixed or layered structure of cellulosic fluff pulp and superabsorbent. The size and absorbent capacity of the absorbent structure may be varied to be suited for different uses such as sanitary articles, panty liners, adult incontinence pads and diapers, baby diapers, pant diapers, etc.

The backsheet 7 may consist of a thin plastic film, e.g., a polyethylene or polypropylene film, a nonwoven material coated with a liquid impervious material, a hydrophobic nonwoven material, which resists liquid penetration. Laminates of plastic films and nonwoven materials may also be used. The backsheet material can be breathable so as to allow vapor to escape from the absorbent structure, while still preventing liquids from passing through the backsheet material.

The elastic elements 12,13 may consist of one or more elastic threads, elastic ribbon, elastic film and/or elastic foam.

As may be seen in the figure, the respective elastic elements 12,13 each extends along at least a part of the front portion 9 and over at least 30% of the intermediate portion 10, such as in this figure almost 90% of the intermediate portion 10, leaving a portion along the intermediate portion of the absorbent core closest to the rear end edge of the absorbent pad free from elastic elements 12,13. The elastic elements 12,13 are arranged at a distance from the longitudinal side edges 8a,8b of the absorbent core 8, such that there is an interspace free from absorbent material located between the absorbent core 8 and the elastic elements 12,13. The elastic elements 12,13 furthermore extend laterally outboard a widest portion in the front portion 9, as seen in a transverse direction T, of the second core layer 28.

The invention claimed is:

1. An absorbent pad comprising a fluid permeable topsheet, a backsheet and an absorbent core being located between the topsheet and the backsheet, the absorbent core having first and second longitudinal side edges and front and rear end edges, the absorbent core having a front portion, a rear portion and an intermediate portion located between the front portion and the rear portion, as seen in a longitudinal direction of the absorbent pad, the absorbent core having a width varying no more than 20 mm along a length of the absorbent core extending in the longitudinal direction of the absorbent pad, the absorbent core includes a first region having a first level of absorbability and a second region surrounding the first region, the second region having a second level of absorbability, wherein the second level of absorbability is less than the first level of absorbability, wherein the topsheet includes a central printed zone, arranged over the front portion, the rear portion and the intermediate portion of the absorbent core, the central printed zone being provided with a first printed pattern comprising first print elements, wherein the topsheet includes a peripheral security printed zone arranged at least over the rear portion of the absorbent core, the peripheral security printed zone being provided with a second printed pattern comprising second print elements, and a majority of the central printed zone is over the first region having the first level of absorbability such that the central printed zone indicates the first level of absorbability, and a majority of the peripheral security printed zone is over the second region having the second level of absorbability such that the peripheral security zone indicates the second level of absorbability, wherein a degree of coverage of the second printed pattern in the peripheral security printed zone is at least 30% greater than a degree of coverage of the first printed pattern in the central printed zone.

2. The absorbent pad according to claim 1, wherein the peripheral security printed zone comprising the second printed pattern extends over the front portion of the absorbent core.

3. The absorbent pad according to claim 2, wherein the peripheral security printed zone extends over the front portion, the intermediate portion and the rear portion outside the central printed zone, thereby framing completely the central printed zone.

4. The absorbent pad according to claim 2, wherein the peripheral security printed zone has a rear end length (l$_r$), as measured along a centre line of the absorbent pad, the rear end length extending in the longitudinal direction between the rear end edge of the absorbent core and a transition between the central printed zone and the peripheral security printed zone arranged over the rear portion of the absorbent core, and a front end length (l$_f$), as measured along a centre line of the absorbent pad, the front end length extending in the longitudinal direction between the front end edge of the absorbent core and a transition between the central printed zone and the peripheral security printed zone arranged over a front portion (9) of the absorbent core, and wherein the $l_r > l_f$.

5. The absorbent pad according to claim 1, wherein the second print elements have a larger mean size than the first printed elements.

6. The absorbent pad according to claim 1, wherein the first printed elements in the central printed zone are absorption enhancement indicating elements.

7. The absorbent pad according to claim 1, wherein the coverage of the first printed pattern in the central printed zone is 5% or more.

8. The absorbent pad according to claim 1, wherein the coverage of the second printed pattern in the peripheral security printed zone is 10% or more.

9. The absorbent pad according to claim 1, wherein the central printed zone has a varying transverse width with a portion arranged in a transitional area of the front portion and the intermediate portion of the core being narrower than the transversal width of the rest of the printed central printed zone and wherein the transverse width in the most narrow section is from 40% to 80% of a widest section of the absorbent core.

10. The absorbent pad according to claim 1, wherein the central printed zone has a varying transverse width with a transition area arranged between the rear portion and the intermediate portion of the core being wider than the transverse width of the rest of the central printed zone.

11. The absorbent pad according to claim 1, wherein the central printed zone is enclosed by a printed contour line(s) following the contour of the printed central printed zone, thereby forming a transition between the central printed zone and the printed peripheral security printed zone.

12. The absorbent pad according to claim 11, wherein the printed contour line(s) comprises a first and a second intermediate printed contour line extending in the longitudinal direction on a respective side of the central printed zone, the first and the second intermediate printed contour line each having a curved shape following the shape of the central printed zone, and the first and the second intermediate printed contour line having a respective first and the second front end portion and a respective first and the second rear end portions.

13. The absorbent pad according to claim 12, wherein the printed contour line(s) includes a U-shaped, modified U-shaped, W-shaped or modified W-shaped contour line rear section enclosing a rear transverse end of the central printed zone and having contour line rear section first and second legs extending at each side of the central printed zone in the longitudinal direction toward the front end edge of the absorbent core.

14. The absorbent pad according to claim 13, wherein the contour line rear section first and second legs are arranged outwardly of, and overlapping with the respective first and the second rear end portion of the first and a second intermediate printed contour line, as seen in the transverse direction.

15. The absorbent pad according to claim 13, wherein the peripheral security printed zone has a rear end length being at least 40% of the length of the rear portion of the absorbent core, as measured along a centre line of the absorbent pad extending in the longitudinal direction between the rear end edge of the absorbent core and the contour line rear section.

16. The absorbent pad according to claim 13, wherein the contour line rear section is provided with a rear end direction indicator.

17. The absorbent pad according to claim 12, wherein the printed contour line(s) include(s) a U-shaped, modified U-shaped, V-shaped or modified V-shaped contour line front section enclosing a front transverse end of the central printed zone and having contour line front section first and second legs extending at each side of the central printed zone toward the rear end edge of the absorbent core.

18. The absorbent pad according to claim 17, wherein the contour line front section first and second legs are arranged outwardly of, and overlapping with the respective first and the second front end portion of the first and a second intermediate printed contour line, as seen in the transverse direction.

19. The absorbent pad according to claim 17, wherein the contour line front section is provided with a front end direction indicator.

20. The absorbent pad according to claim 1, wherein the backsheet is provided with adhesive means on a garment-facing side thereof.

21. The absorbent pad according to claim 1, wherein the absorbent pad is an over-night absorbent pad.

22. The absorbent pad according to claim 1, wherein the absorbent core has a first core layer and a second core layer, the second core layer being located between the topsheet and the first core layer.

23. The absorbent pad according to claim 22, wherein the second core has a length which is shorter than a length of the first core layer, and the second core layer has first and second longitudinal side edges that are laterally inwards of the first and second longitudinal side edges of the first core layer, such as to define the first region having the first level of absorbability and the second region having the second level of absorbability.

* * * * *